US012624188B2

(12) United States Patent
Kim et al.

(10) Patent No.: US 12,624,188 B2
(45) Date of Patent: May 12, 2026

(54) METHOD FOR PRODUCING BIS-2-HYDROXYETHYL TEREPHTHALATE THROUGH CONTINUOUS DEPOLYMERIZATION

(71) Applicant: SK CHEMICALS CO., LTD., Seongnam-si (KR)

(72) Inventors: Ji-Hun Kim, Seongnam-si (KR); Kwang-Woo Park, Seongnam-si (KR); Seong-Ki Lee, Seongnam-si (KR); Joong Ki Lee, Seongnam-si (KR); Yuntae Jin, Seongnam-si (KR)

(73) Assignee: SK CHEMICALS CO., LTD., Seongnam-si (KR)

( * ) Notice: Subject to any disclaimer, the term of this patent is extended or adjusted under 35 U.S.C. 154(b) by 0 days.

(21) Appl. No.: 18/689,150

(22) PCT Filed: Jun. 15, 2023

(86) PCT No.: PCT/KR2023/008268
§ 371 (c)(1),
(2) Date: Mar. 5, 2024

(87) PCT Pub. No.: WO2024/014723
PCT Pub. Date: Jan. 18, 2024

(65) Prior Publication Data
US 2024/0270928 A1     Aug. 15, 2024

(30) Foreign Application Priority Data

Jul. 11, 2022     (KR) ........................ 10-2022-0085160

(51) Int. Cl.
*C08J 11/24*          (2006.01)
*C07C 67/56*          (2006.01)
*C07C 69/82*          (2006.01)
(52) U.S. Cl.
CPC ............... *C08J 11/24* (2013.01); *C07C 67/56* (2013.01); *C07C 69/82* (2013.01)
(58) Field of Classification Search
CPC ....... C08J 11/24; C08J 2367/02; C07C 67/56; C07C 69/82; C07C 67/03; Y02W 30/62
See application file for complete search history.

(56) References Cited

U.S. PATENT DOCUMENTS

2019/0161595 A1*   5/2019   Charra ................... C07C 67/54
2021/0040287 A1    2/2021   Fang et al.

FOREIGN PATENT DOCUMENTS

| | | | |
|---|---|---|---|
| EP | 3765560 | A1 | 1/2021 |
| JP | 2002-332379 | * | 11/2002 |
| JP | 2002-332379 | A | 11/2002 |
| JP | 2003-055300 | * | 2/2003 |
| JP | 2003-055300 | A | 2/2003 |
| JP | 2021-532197 | A | 11/2021 |
| KR | 2002-0077874 | A | 10/2002 |
| KR | 10-2012-0128480 | A | 11/2012 |
| KR | 10-2019-0026737 | A | 3/2019 |
| KR | 10-2021-0066507 | A | 6/2021 |
| KR | 10-2021-0067554 | A | 6/2021 |
| KR | 10-2022-0068991 | A | 5/2022 |
| KR | 10-2504202 | B1 | 2/2023 |
| WO | 2020/149798 | A1 | 7/2020 |
| WO | 2021/028695 | A1 | 2/2021 |
| WO | 2021/214642 | A1 | 10/2021 |

OTHER PUBLICATIONS

JP2003-055300 translation (Year: 2003).*
JP2002-332379 translation (Year: 2002).*
Korean Intellectual Office Notice of Preliminary Rejection for 10-2022-0085160 dated Nov. 22, 2022.
Korean Intellectual Office Notice of Allowance for KR Application No. 10-2022-0085160 dated Feb. 2, 2023.
International Search Report for PCT/KR2023/008268 dated Sep. 12, 2023 (PCT/ISA/210).
Office Action issued May 27, 2025 in Japanese Application No. 2024-525115.

* cited by examiner

*Primary Examiner* — Andrew D Kosar
*Assistant Examiner* — Blaine G Doletski
(74) *Attorney, Agent, or Firm* — Sughrue Mion, PLLC

(57)          ABSTRACT

A method for producing bis-2-hydroxyethyl terephthalate is disclosed. The method includes the steps of: (1) adding a waste polyester raw material into a co-extruder to obtain a co-extrudate; (2) adding the co-extrudate into a reactor with an agitation shaft and depolymerizing same to obtain a first reaction product; (3) adding the first reaction product into a first continuous stirred tank reactor and depolymerizing same to obtain a second reaction product; and (4) adding the second reaction product into a second continuous stirred tank reactor and depolymerizing same to obtain a third reaction product.

15 Claims, 3 Drawing Sheets

[Fig. 1]
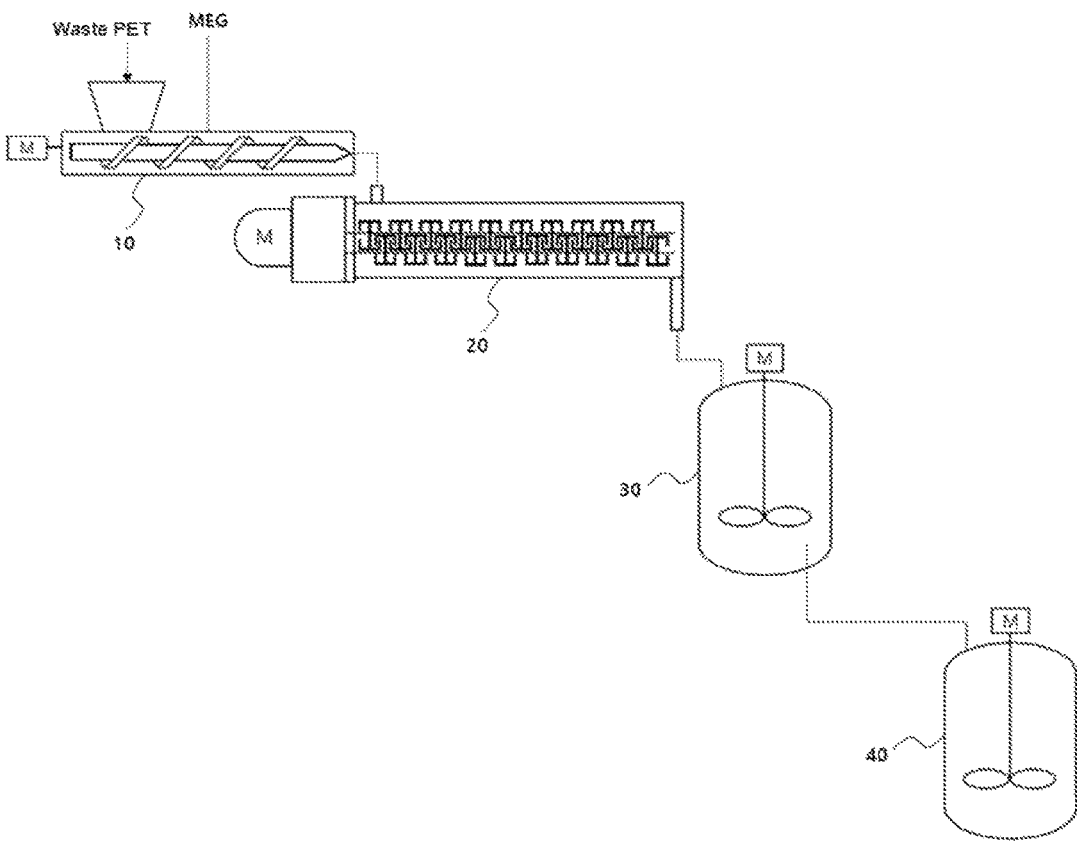

[Fig. 2]
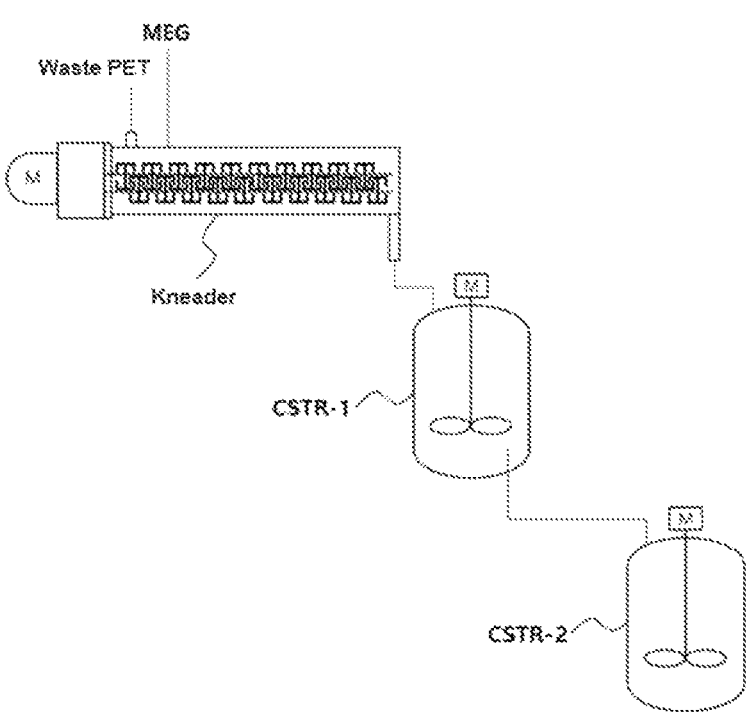

[Fig. 3]
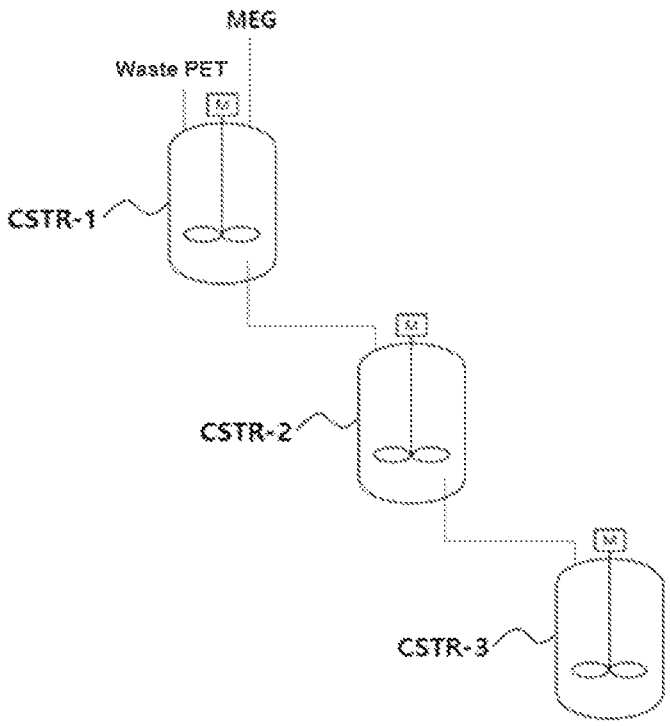

METHOD FOR PRODUCING BIS-2-HYDROXYETHYL TEREPHTHALATE THROUGH CONTINUOUS DEPOLYMERIZATION

CROSS REFERENCE TO RELATED APPLICATIONS

This application is a National Stage of International Application No. PCT/KR2023/008268 filed Jun. 15, 2023, claiming priority based on Korean Patent Application No. 10-2022-0085160 filed Jul. 11, 2022.

TECHNICAL FIELD

The present invention relates to a process for preparing bis(2-hydroxyethyl) terephthalate (BHET) with high purity in high efficiency using waste polyester.

BACKGROUND ART

Polyester among polymers is used as a material in various fields by virtue of its excellent mechanical strength, thermal resistance, transparency, and gas barrier properties. In particular, polyester sheets or plates have good transparency and excellent mechanical strength, so that they are widely used for cases, boxes, partitions, shelves, panels, packaging materials, building materials, interior and exterior materials, and the like.

As a result, waste of plastics such as polyester is generated globally at an unmanageable level every year. Recently, countries around the world are preparing regulations and plans for recycling waste plastic resources, including waste polyester.

Although physical and chemical methods are used as methods of recycling waste polyester, physical recycling methods cannot guarantee purity and, thus, are not widely used. Meanwhile, in chemical recycling methods, the ester bond of waste polyester is cleaved to depolymerize it. Reactions such as glycolysis, hydrolysis, methanolysis, and aminolysis are used. Glycolysis among them is to decompose waste polyester by adding a glycol such as ethylene glycol or diethylene glycol at high temperatures. A reaction product mainly containing bis(2-hydroxyethyl) terephthalate (BHET) is obtained. The bis(2-hydroxyethyl) terephthalate contained in the reaction product may be used as a raw material for preparing unsaturated polyester or ester polyol after the crystallization or purification thereof.

In order to use bis(2-hydroxyethyl) terephthalate as the above raw material, it is necessary to increase the purity of bis(2-hydroxyethyl) terephthalate by minimizing the formation of by-products such as diethylene glycol esters (DEG esters) during the depolymerization process. To this end, a method of performing depolymerization by designing continuous stirred tank reactor (CSTRs) in multiple stages is currently adopted.

However, this method has a problem in that the process efficiency is reduced since the time required to depolymerize waste polyester is twice or more the case in which a batch reactor is used. In addition, the formation of by-products is not well controlled in the process of depolymerizing waste polyester; thus, there is a limit to obtaining bis(2-hydroxyethyl) terephthalate having a desired purity.

PRIOR ART DOCUMENT

Patent Document (Patent Document 1) Korean Laid-open Patent Publication No. 2022-0068991

DISCLOSURE OF INVENTION

Technical Problem

The present inventors have conducted various studies in order to solve the above-mentioned conventional problems. As a result, it has been discovered that, as waste polyester is subjected to a reduction in molecular weight and short-term depolymerization prior to the depolymerization through a continuous reactor (CSTR), bis(2-hydroxyethyl) terephthalate with high purity can be prepared in high efficiency (increased productivity).

Accordingly, an object of the present invention is to provide a process for preparing bis(2-hydroxyethyl) terephthalate by continuous depolymerization of waste polyester, in which the purity and production efficiency (productivity) of bis(2-hydroxyethyl) terephthalate can be enhanced.

Solution to Problem

In order to accomplish the above object, the present invention provides a process for preparing bis(2-hydroxyethyl) terephthalate, which comprises (1) feeding a waste polyester raw material to a co-extruder to obtain a co-extrudate; (2) feeding the co-extrudate to an agitated shaft reactor and depolymerizing it to obtain a first reactant; (3) feeding the first reactant to a first continuous reactor and depolymerizing it to obtain a second reactant; and (4) feeding the second reactant to a second continuous reactor and depolymerizing it to obtain a third reactant.

Advantageous Effects of Invention

According to the preparation process of the present invention, waste polyester is subjected to a reduction in molecular weight through co-extrusion and short-term depolymerization with an agitated shaft reactor, followed by depolymerization through continuous reactors (CSTRs) in multiple stages; thus, it is possible to prepare (produce) bis(2-hydroxyethyl) terephthalate (BHET) in a relatively short period of time while minimizing the formation of by-products (e.g., DEG and DEG esters) considered as impurities.

Accordingly, the present invention can provide bis(2-hydroxyethyl) terephthalate (BHET) with high purity in high efficiency, and the bis(2-hydroxyethyl) terephthalate (BHET) prepared as described above can be used as a raw material to prepare a polyester having excellent quality and a product using the same.

BRIEF DESCRIPTION OF DRAWINGS

FIG. 1 illustrates an example of the process for preparing bis(2-hydroxyethyl) terephthalate according to an embodiment of the present invention.

FIG. 2 illustrates the process for preparing bis(2-hydroxy-ethyl) terephthalate according to Comparative Examples 1 to 3.

FIG. 3 illustrates the process for preparing bis(2-hydroxy-ethyl) terephthalate according to Comparative Examples 4 to 6.

BEST MODE FOR CARRYING OUT THE INVENTION

Hereinafter, the present invention will be described in detail. The present invention herein is not limited to the disclosures given below, but it may be modified into various forms as long as the gist of the invention is not changed.

In the present specification, the term "comprising" is intended to specify a particular characteristic, region, step, process, element, and/or component. It does not exclude the presence or addition of any other characteristic, region, step, process, element and/or component, unless specifically stated to the contrary.

Throughout the present specification, the terms first, second, and the like are used for the purpose of distinguishing one element from another. But the components should not be limited by the terms.

All numbers and expressions related to the quantities of components, reaction conditions, and the like used herein are to be understood as being modified by the term "about" unless otherwise indicated.

The number average molecular weight and weight average molecular weight of a compound (reactant or product) described in the present specification is a relative mass based on carbon-12 ($^{12}$C) as is well known. Although its unit is not described, it may be understood as a molar mass (g/mole) of the same numerical value, if necessary.

For the sake of description, the sizes of individual elements in the appended drawings may be exaggeratedly depicted, and they may differ from the actual sizes.

Process for Preparing bis(2-hydroxyethyl) terephthalate

The present invention relates to a process for preparing bis(2-hydroxyethyl) terephthalate, one of the raw materials for preparing recycled resins (post-consumer resins), through the depolymerization of waste polyester. The present invention is characterized in that waste polyester is subjected to a reduction in molecular weight and short-term depolymerization, followed by depolymerization in multiple stages through continuous reactors.

Specifically, the process for preparing bis(2-hydroxy-ethyl) terephthalate according to the present invention comprises (1) feeding a waste polyester raw material to a co-extruder to obtain a co-extrudate; (2) feeding the co-extrudate to an agitated shaft reactor and depolymerizing it to obtain a first reactant; (3) feeding the first reactant to a first continuous reactor and depolymerizing it to obtain a second reactant; and (4) feeding the second reactant to a second continuous reactor and depolymerizing it to obtain a third reactant.

The process for preparing bis(2-hydroxyethyl) terephthalate according to the present invention may further comprise (5) purifying the third reactant of step (4).

Hereinafter, each step of the process will be described in detail with reference to FIG. 1, as follows.

Step (1): Obtaining a Co-Extrudate

According to the present invention, in step (1), a waste polyester raw material is fed to a co-extruder (10) to obtain a co-extrudate. Specifically, in step (1), the reduction in molecular weight of the waste polyester raw material is achieved in a physical and/or chemical way through the co-extruder (10).

The waste polyester raw material may be obtained from a polyester material product discarded after use. Specifically, the waste polyester may be obtained by pretreating waste products such as beverage bottles, fabrics, films, cases, boxes, partitions, shelves, protective panels, packaging materials, building materials, and interior and exterior materials, which comprise various polyester materials (e.g., poly-ethylene terephthalate (PET) material) discarded after having been used by consumers.

The pretreatment may be carried out by removing other plastics, metals, and foreign substances mixed in the waste, washing it, and then crushing it through a crusher. As a result of the pretreatment, the waste polyester raw material may have a flake form. In addition, the waste polyester raw material may have a fine structure like a fiber.

In step (1), a first glycol-based compound may be continuously fed to the co-extruder (10). As the first glycol-based compound is fed to the co-extruder (10), the molecular weight of the waste polyester raw material can be reduced more efficiently.

The first glycol-based compound is not particularly limited. Specifically, it may be at least one selected from the group consisting of ethylene glycol (monoethylene glycol), propylene glycol, and diethylene glycol.

The feeding amount of the first glycol-based compound may be 0.01 to 100 parts by weight, 1 to 80 parts by weight, 3 to 60 parts by weight, or 5 to 50 parts by weight, relative to 100 parts by weight of the waste polyester raw material. As the feeding amount of the first glycol-based compound is within the above range, the molecular weight of the waste polyester raw material can be reduced through the co-extruder (10) to the maximum.

Meanwhile, the co-extrusion may be carried out at 170 to 290° C., specifically, 173 to 275° C., 175 to 250° C., 180 to 230° C., 185 to 215° C., or 190 to 200° C. As the co-extrusion is carried out within the above temperature range, the molecular weight of the waste polyester raw material can be reduced stably. In addition, the extrusion speed (screw rpm) during the co-extrusion may be 130 to 250 rpm, 135 to 220 rpm, 140 to 200 rpm, or 145 to 185 rpm.

The co-extruder (10) may not be particularly limited as long as it is designed to co-extrude the waste polyester raw material. Specifically, the co-extruder (10) may be a single-screw co-extruder or a multi-screw (e.g., twin-screw) co-extruder conventionally known.

The co-extrudate obtained through step (1) may have a relatively low weight average molecular weight and number average molecular weight. That is, the co-extrudate may have a weight average molecular weight of 3,000 to 36,000, specifically, 3,500 to 30,000, 3,800 to 25,000, or 4,000 to 20,000. In addition, the co-extrudate may have a number average molecular weight of 500 to 10,000, 800 to 8,000, 1,000 to 6,500, or 1,100 to 5,500.

As the co-extrudate obtained through step (1) has a relatively low molecular weight as described above, the time to be spent in the depolymerization procedure in steps (2) to (4) can be shortened while the formation of by-products (e.g., DEG and DEG esters) is minimized.

Step (2): Obtaining a First Reactant Through an Agitated Shaft Reactor

According to the present invention, in step (2), the co-extrudate is fed to an agitated shaft reactor and depolymerized (first depolymerization) to obtain a first reactant. Specifically, in step (2), a glycolysis reaction in which polymer chains and the like present in the co-extrudate are decomposed by the first glycol-based compound can be carried out within a short time.

If the first glycol-based compound is not fed to the co-extruder (10) in step (1), the first glycol-based compound may be continuously fed to the agitated shaft reactor (20).

In order to facilitate the depolymerization of the co-extrudate through the agitated shaft reactor (20), a catalyst for facilitating the depolymerization reaction may be further fed to the agitated shaft reactor (20). The catalyst is not particularly limited as long as it is a commonly known catalyst. Specifically, it may be a catalyst comprising a metal acetate, an anhydride of the acetate, or a hydrate of the acetate. More specifically, the catalyst may be an acetate of at least one selected from the group consisting of zinc acetate, sodium acetate, cobalt acetate, and manganese acetate, or a hydrate or anhydride thereof.

The amount of the catalyst fed to the agitated shaft reactor (20) may be 0.01 to 5 parts by weight, 0.1 to 3 parts by weight, or 0.2 to 1 part by weight, relative to 100 parts by weight of the waste polyester raw material.

The depolymerization of the co-extrudate may be carried out at 180 to 210° C. (specifically, 183 to 208° C., 185 to 205° C., 186 to 204° C., 188 to 203° C., 190 to 200° C., or 193 to 198° C.) for 50 minutes or shorter (specifically, 5 to 50 minutes, 10 to 50 minutes, 20 to 50 minutes, 22 to 45 minutes, 25 to 40 minutes, or 30 to 35 minutes). In particular, the depolymerization temperature of the co-extrudate may be higher than the depolymerization temperature in steps (3) and (4), and the time spent for depolymerization may be shorter than the time to be spent for depolymerization in steps (3) and (4). As a result, bis(2-hydroxyethyl) terephthalate with high purity can be prepared in high efficiency.

Meanwhile, the agitated shaft reactor (20) may not be particularly limited as long as it is designed to mix the co-extrudate, the first glycol-based compound, and the catalyst. Specifically, the agitated shaft reactor (20) may comprise at least one selected from the group consisting of a kneader, a paddle mixer, a plow shear mixer, a screw mixer, and a ribbon blender. More specifically, it may be a kneader or a paddle mixer.

The first reactant obtained through step (2) may have a peak area fraction of bis(2-hydroxyethyl) terephthalate (BHET) of 50 to 75%, specifically, 55 to 75%, 58 to 73%, or 65 to 70%, when analyzed by high-performance liquid chromatography (HPLC).

In addition, the first reactant may have a peak area fraction of oligomers having a weight average molecular weight of less than 2,000 (>Mw 2,000) of 11.0% or less, specifically, 0.5 to 10.5%, 0.8 to 10%, 1.0 to 8.0%, 1.3 to 7.5%, or 1.5 to 7.3%, when analyzed by gel permeation chromatography (GPC).

Step (3): Obtaining a Second Reactant Through a First Continuous Reactor

According to the present invention, in step (3), the first reactant is fed to a first continuous reactor and depolymerized (second depolymerization) to obtain a second reactant. Specifically, in step (3), a second glycol-based compound may be continuously fed to a first continuous reactor (30) as well. As a result, a glycolysis reaction in which polymer chains and the like present in the first reactant are decomposed by the second glycol-based compound can be carried out.

The second glycol-based compound is not particularly limited. Specifically, it may be at least one selected from the group consisting of ethylene glycol (monoethylene glycol), propylene glycol, and diethylene glycol.

The amount of the second glycol-based compound fed to the first continuous reactor (30) may be 50 to 340 parts by weight relative to 100 parts by weight of the first reactant. Specifically, the second glycol-based compound may be continuously fed to the first continuous reactor (30) in an amount of 50 to 300 parts by weight, 50 to 250 parts by weight, 50 to 200 parts by weight, or 50 to 100 parts by weight, relative to 100 parts by weight of the first reactant. As the feeding amount of the second glycol-based compound is within the above range, the depolymerization of the first reactant can be efficiently carried out, whereby the ratio of oligomers, dimers, or trimers contained in the second reactant obtained through step (3) can be significantly reduced.

The depolymerization of the first reactant may be carried out at 170 to 195° C. (specifically, 173 to 194° C., 175 to 193° C., 177 to 192° C., 180 to 191° C., 183 to 191° C., or 185 to 190° C.) for 30 to 50 minutes (specifically, 32 to 45 minutes, 35 to 43 minutes, or 38 to 40 minutes). As the depolymerization of the first reactant is carried out under the above conditions, the depolymerization is efficiently performed and the overall process time is shortened, whereby it is possible to enhance the purity and preparation efficiency (productivity) of bis(2-hydroxyethyl) terephthalate.

The depolymerization of the first reactant may be carried out in the presence of the catalyst continuously fed to the agitated shaft reactor (20) in step (2) or a catalyst directly fed to the first continuous reactor (30). The catalyst may be a catalyst comprising a metal acetate, an anhydride thereof, or a hydrate thereof.

Meanwhile, the first continuous reactor (30) may not be particularly limited as long as it is a conventional continuous flow tank reactor designed to carry out depolymerization.

The second reactant obtained through step (3) may have a peak area fraction of bis(2-hydroxyethyl) terephthalate (BHET) of 50 to 85%, specifically, 55 to 84%, 65 to 83.5%, or 75 to 83%, when analyzed by high-performance liquid chromatography (HPLC). Here, the HPLC peak area fraction of bis(2-hydroxyethyl) terephthalate (BHET) in the second reactant may vary depending on the amount of the second glycol-based compound fed to the first continuous reactor (30).

Step (4): Obtaining a Third Reactant Through a Second Continuous Reactor

According to the present invention, in step (4), the second reactant is fed to a second continuous reactor (40) and depolymerized (third depolymerization) to obtain a third reactant. Specifically, in step (4), a glycolysis reaction in which polymer chains and the like present in the second reactant are decomposed by the unreacted second glycol-based compound, which is discharged from the first continuous reactor (30) of step (1) and supplied to the second continuous reactor (40), can be carried out. A third glycol-based compound may be additionally fed to the second continuous reactor (40) in preparation for a decrease in the depolymerization efficiency when the unreacted second glycol-based compound is not supplied to the second continuous reactor (40) to the extent that the depolymerization is sufficiently carried out, or when the purity of the unreacted second glycol-based compound is lowered.

The third glycol-based compound is not particularly limited. Specifically, it may be at least one selected from the group consisting of ethylene glycol (monoethylene glycol), propylene glycol, and diethylene glycol.

The amount of the third glycol-based compound fed to the second continuous reactor (40) may be 50 to 150 parts by weight relative to 100 parts by weight of the second reactant. Specifically, the third glycol-based compound may be continuously fed to the second continuous reactor (40) in an amount of 50 to 130 parts by weight, 55 to 110 parts by weight, 60 to 90 parts by weight, or 65 to 80 parts by weight, relative to 100 parts by weight of the second reactant. As the feeding amount of the third glycol-based compound is within the above range, the depolymerization of the second reactant can be efficiently carried out, whereby the ratio of oligomers, dimers, or trimers contained in the third reactant obtained through step (4) can be significantly reduced.

The depolymerization of the second reactant may be carried out at 140 to 170° C. (specifically, 143 to 168° C., 145 to 165° C., 148 to 160° C., 149 to 158° C., or 150 to 155° C.) for 30 to 50 minutes (specifically, 35 to 45 minutes, 38 to 43 minutes, or 40 to 42 minutes). As the depolymerization of the second reactant is carried out under the above conditions, the depolymerization is efficiently performed and the overall process time is shortened, whereby it is possible to enhance the purity and preparation efficiency (productivity) of bis(2-hydroxyethyl) terephthalate.

The depolymerization of the second reactant may be carried out in the presence of the catalyst continuously fed to the agitated shaft reactor (20) in step (2), the catalyst continuously fed to the first continuous reactor (30), or a catalyst directly fed to the second continuous reactor (40). The catalyst may be a catalyst comprising a metal acetate, an anhydride thereof, or a hydrate thereof.

Meanwhile, the second continuous reactor (40) may not be particularly limited as long as it is a conventional continuous flow tank reactor designed to carry out depolymerization.

The third reactant obtained through step (4) may have a peak area fraction of bis(2-hydroxyethyl) terephthalate (BHET) of 80 to 90%, specifically, 83.5 to 90%, 84 to 89.5%, or 84.5 to 89%, when analyzed by high-performance liquid chromatography (HPLC).

In addition, the third reactant may have a peak area fraction of oligomers having a weight average molecular weight of less than 2,000 (>Mw 2,000) of 2.0% or less, specifically, 0.0 to 2.0%, 0.0 to 1.8%, 0.0 to 1.7%, 0.0 to 1.5%, or 0.0 to 1.0%, when analyzed by gel permeation chromatography (GPC).

Meanwhile, the third reactant is subjected to a filtration step to remove unreacted materials and impurities (contaminants). In such an event, since the third reactant contains almost no oligomers, which have a significant impact on the time required for the filtration step, the present invention can carry out the filtration step in a relatively short time. That is, in the present invention, prior to depolymerization in multiple stages by directly feeding waste polyester to a continuous reactor, the molecular weight of the waste polyester raw material is reduced through the co-extruder (10) in step (1), and the reactant obtained by carrying out short-term depolymerization through the agitated shaft reactor (20) in step (2) is subjected to depolymerization in multiple stages; thus, the third reactant obtained through the final depolymerization may contain almost no oligomers that would otherwise increase the time for filtration or delay the filtration step. In addition, as multi-stage depolymerization is carried out through steps (3) and (4) described above, the residence time for high-temperature reaction of the reactant obtained in each step is shortened, and the formation of by-products is minimized; thus, it is possible to prepare bis(2-hydroxy-ethyl) terephthalate with high purity in high yield.

Specifically, when the third reactant is filtered using a filtration membrane having a pore size of 0.1 μm, the flow rate (filtering flow rate) passing through the filtration membrane may be 10 kg/hr or more, specifically, 10 to 100 kg/hr, 12 to 90 kg/hr, 13 to 80 kg/hr, or 14 to 70 kg/hr. As the flow rate is within the above range, the preparation efficiency (productivity) of bis(2-hydroxyethyl) terephthalate can be remarkably increased.

In addition, the third reactant may have a filtration loss rate of less than 8% by weight according to the following Equation 1, specifically, 0.1 to 7.5% by weight, 0.5 to 7.0% by weight, 1.0 to 6.0% by weight, or 1.3 to 5.0% by weight.

$$\text{Filtration loss rate (\% by weight)} = (m_1 - m_2/m_1) \times 100 \quad \text{[Equation 1]}$$

$m_1$: Initial weight of the third reactant $m_2$: Weight of the third reactant that has passed through the filtration membrane having a pore size of 0.1 μm Step (5): Purification of the Third Reactant According to the present invention, in step (5), the third reactant is purified. Step (5) may be optionally carried out as needed.

The purification of the third reactant may be carried out through a commonly known process. Specifically, the purification may comprise one or more steps of filtration, ion exchange, distillation, decolorization, and adsorption.

The filtration step may comprise a process such as membrane filtration, filter aid filtration, reduced pressure flash (cooling), and solid-liquid separation. As such a filtration step is carried out, it is possible to remove particulates and insoluble foreign substances contained in the third reactant.

The ion exchange is a step carried out using a commonly known ion-exchange resin. The ion-exchange resin may comprise a cation-exchange resin, an anion-exchange resin, an amphoteric ion-exchange resin, a chelate resin, or the like. Specifically, the cation-exchange resin may be a strongly acidic cation-exchange resin having a sulfonic acid group (—SO₃H) or a weakly acidic cation-exchange resin having a carboxyl group (—COOH). The anion-exchange resin may be a strongly basic anion-exchange resin in the form of a quaternary ammonium salt or a weakly basic anion-exchange resin having an amino group. As such an ion-exchange step is carried out, it is possible to remove catalysts and metal foreign substances.

The distillation may comprise a step such as vacuum distillation, thin film evaporation, falling film evaporation, and short path evaporation. As such a distillation step is carried out, it is possible to remove unreacted glycol-based compounds.

The decolorization is a step carried out using a commonly known decolorizing agent. Specifically, the decolorizing agent may comprise activated carbon, activated clay, diatomaceous earth, and the like. As such a decolorization step is carried out, it is possible to remove colored substances.

The adsorption is a step carried out using a conventionally known adsorbent. As such an adsorption step is carried out, it is possible to remove other foreign substances to obtain a crystallized final reactant (bis(2-hydroxyethyl) terephthalate).

MODE FOR THE INVENTION

Hereinafter, the present invention will be described in more detail with reference to embodiments. However, these examples are provided only for illustration purposes, and the present invention is not limited thereto.

Preparation Example 1

Crushed waste PET (PET in the form of flakes) and monoethylene glycol (MEG) were fed to a single-screw co-extruder at a feeding rate of 15.5 kg/hr, respectively, and co-extruded (for a reduction in molecular weight) at a temperature of 180° C. and 150 rpm to obtain a co-extrudate.

Preparation Examples 2 to 7

Each co-extrudate was obtained through the same procedure as in Preparation Example 1, except that the feeding rate and co-extrusion conditions were adjusted as shown in Table 1 below.

Test Example 1

The co-extrudates obtained in Preparation Examples 1 to 7 were each analyzed by gel permeation chromatography (GPC) under the following conditions. The results are shown in Table 1 below.

GPC analysis equipment: HLC-8420GPC Elite of TOSOH

Mobile phase: chloroform/phenol-based mixture

Temperature: 40° C.

Column: individual gel type×4 EA

Sample pretreatment: a chloroform/phenol-based mixture solvent was used to adjust the sample concentration in the solution to 0.5 wt/v %.

The second reactant thus obtained and additional monoethylene glycol (MEG-3) (feeding rate: 31.0 kg/hr) were fed to the second continuous reactor (CSTR-1), and a third depolymerization reaction was carried out at 150° C. for 40 minutes to obtain a third reactant.

The third reactant thus obtained was purified by a conventional method to prepare bis(2-hydroxyethyl) terephthalate.

Examples 2 to 71 Application of a Co-Extruder, a Kneader, a First Continuous Reactor, and a Second Continuous Reactor Bis(2-hydroxyethyl) terephthalate was prepared in the same manner as in Example 1, except that the feeding rate and reaction temperature in each depolymerization reaction were adjusted as shown in Table 2 below.

Comparative Examples 1 to 31 Application of a Kneader, a First Continuous Reactor, and a Second Continuous Reactor According to the design conditions of FIG. 2, depolymerization of crushed waste PET (PET in the form of flakes) was carried out continuously through a kneader, a first continuous reactor (CSTR-1), and a second continuous reactor (CSTR-2) in the presence of a zinc acetate anhydride catalyst, without a co-extrusion process of the crushed waste PET. Bis(2-hydroxyethyl) terephthalate was prepared while the feeding rate and reaction temperature in each depolymerization reaction were adjusted as shown in Table 3 below.

TABLE 1

| | | Prep. Ex. 1 | Prep. Ex. 2 | Prep. Ex. 3 | Prep. Ex. 4 | Prep. Ex. 5 | Prep. Ex. 6 | Prep. Ex. 7 |
|---|---|---|---|---|---|---|---|---|
| Feeding rate (kg/hr) | PET | 15.5 | 18.6 | 21.7 | 24.8 | 27.9 | 29.5 | 31.0 |
| | MEG | 15.5 | 12.4 | 9.3 | 6.2 | 3.1 | 1.6 | 0.0 |
| | Ratio (MEG/PET) | 1.0 | 0.67 | 0.43 | 0.25 | 0.11 | 0.05 | 0.00 |
| Co-extrusion condition | Barrel temp. (° C.) | 180 | 190 | 195 | 210 | 245 | 250 | 290 |
| | Screw rpm | 150 | 150 | 150 | 150 | 150 | 180 | 220 |
| GPC (Da) | Mn | 1,180 | 2,772 | 3,052 | 2,210 | 3,255 | 5,190 | 8,980 |
| | Mw | 4,810 | 12,926 | 15,292 | 18,762 | 19,410 | 19,980 | 34,560 |
| | PD (Mw/Mn) | 4.08 | 4.66 | 5.01 | 8.49 | 5.96 | 3.85 | 3.85 |

[Example 1] Application of a Co-Extruder, a Kneader, a First Continuous Reactor, and a Second Continuous Reactor According to the design conditions of FIG. 1, depolymerization was carried out continuously through a kneader, a first continuous reactor (CSTR-1), and a second continuous reactor (CSTR-2), following the co-extrusion process of Preparation Example 1. Specifically, the co-extrudate of Preparation Example 1 (feeding rate: 31.0 kg/hr) and zinc acetate anhydride (feeding rate: 0.065 kg/hr) as a catalyst were fed to a kneader, and a first depolymerization reaction was carried out at 195° C. for 35 minutes to obtain a first reactant.

The first reactant thus obtained and additional monoethylene glycol (MEG-2) (feeding rate: 15.5 kg/hr) were fed to the first continuous reactor (CSTR-1), and a second depolymerization reaction was carried out at 190° C. for 40 minutes to obtain a second reactant.

Comparative Examples 4 to 61 Application of a First Continuous Reactor, a Second Continuous Reactor, and a Third Continuous Reactor According to the design conditions of FIG. 3, depolymerization of crushed waste PET (PET in the form of flakes) was carried out continuously through a first continuous reactor (CSTR-1), a second continuous reactor (CSTR-2), and a third continuous reactor (CSTR-3) in the presence of a zinc acetate anhydride catalyst, without a co-extrusion process and depolymerization through a kneader of the crushed waste PET. Bis(2-hydroxyethyl) terephthalate was prepared while the feeding rate and reaction temperature in each depolymerization reaction were adjusted as shown in Table 3 below.

TABLE 2

|  |  | Ex. 1 | Ex. 2 | Ex. 3 | Ex. 4 | Ex. 5 | Ex. 6 | Ex. 7 |
|---|---|---|---|---|---|---|---|---|
| Feeding rate (kg/hr) | Prep. Ex. 1 co-extrudate | 31.0 | 31.0 | — | — | — | — | — |
|  | Prep. Ex. 3 co-extrudate | — | — | 31.0 | 31.0 | — | — | — |
|  | Prep. Ex. 5 co-extrudate | — | — | — | — | 31.0 | 31.0 | — |
|  | Prep. Ex. 7 co-extrudate | — | — | — | — | — | — | 15.5 |
|  | MEG-1 (fed to kneader) | 0.0 | 0.0 | 0.0 | 0.0 | 0.0 | 0.0 | 31.0 |
|  | MEG-2 (fed to CSTR-1) | 15.5 | 46.5 | 34.1 | 77.5 | 52.7 | 15.5 | 31.0 |
|  | MEG-3 (fed to CSTR-2) | 31.0 | 0.0 | 43.4 | — | 55.8 | 31.0 | 62.0 |
|  | Catalyst | 0.065 | 0.065 | 0.091 | 0.091 | 0.117 | 0.117 | 0.130 |
| Reaction (residence) temp. (° C.) | Kneader | 195 | 195 | 195 | 195 | 195 | 195 | 195 |
|  | CSTR-1 | 190 | 190 | 190 | 190 | 190 | 190 | 190 |
|  | CSTR-2 | 150 | 150 | 150 | 150 | 150 | 150 | 150 |

TABLE 3

|  |  | C. Ex. 1 | C. Ex. 2 | C. Ex. 3 | C. Ex. 4 | C. Ex. 5 | C. Ex. 6 |
|---|---|---|---|---|---|---|---|
| Feeding rate (kg/hr) | Crushed waste PET | 15.5 | 15.5 | 15.5 | 15.5 | 15.5 | 15.5 |
|  | MEG-1 (fed to kneader) | 15.5 | 31.0 | 62.0 | — | — | — |
|  | MEG-2 (fed to CSTR-1) | 15.5 | 0.0 | 0.0 | 15.5 | 31.0 | 62.0 |
|  | MEG-3 (fed to CSTR-2) | 31.0 | 31.0 | 0.0 | 15.5 | 0.0 | 0.0 |
|  | MEG-4 (fed to CSTR-3) | — | — | — | 31.0 | 31.0 | 0.0 |
|  | Catalyst | 0.065 | 0.065 | 0.065 | 0.065 | 0.065 | 0.065 |
| Reaction (residence) temp. (° C.) | Kneader | 195 | 195 | 195 | — | — | — |
|  | CSTR-1 | 190 | 190 | 190 | 195 | 195 | 195 |
|  | CSTR-2 | 150 | 150 | 150 | 190 | 190 | 190 |
|  | CSTR-3 | — | — | — | 150 | 150 | 150 |

Test Example 2

The reactants obtained in Examples 1 to 7 and Comparative Examples 1 to 6 were each analyzed by gel permeation chromatography (GPC) under the following conditions. The results are shown in Tables 4 and 5 below.

GPC analysis equipment: HLC-8420GPC Elite of TOSOH

Mobile phase: chloroform/phenol-based mixture

Temperature: 40° C.

Column: individual gel type×4 EA

Sample pretreatment: a chloroform/phenol-based mixture solvent was used to adjust the sample concentration in the solution to 0.5 wt/v %.

Test Example 31

The third reactant obtained through depolymerization in the second continuous reactor (CSTR-2) in Examples 1 to 7 and Comparative Examples 1 to 3 and the third reactant obtained through depolymerization in the third continuous reactor (CSTR-3) in Comparative Examples 4 to 6 were each filtered through a circular glass fiber filter, and the filtering time and flow rate were measured. The results are shown in Tables 4 and 5 below. Here, the evaluation conditions and evaluation criteria were as follows.

Pore size of the glass fiber filter: 0.1 μm
Diameter of the glass fiber filter: 320 mm
Filtering temperature: 100 to 150° C.
Whether filtering was successful—⊚: filtering time within 20 minutes; ○: filtering time exceeding 20 minutes to 60 minutes; x: filtering time exceeding 60 minutes Test Example 4

The reactants (filtrates) obtained in Test Example 3 were each analyzed by high-performance liquid chromatography (HPLC) under the following conditions. The results are shown in Tables 4 and 5 below.
Pretreatment: About 0.01 g of a sample was diluted in about 20 ml of methanol and then measured by HPLC.
HPLC analysis equipment (model): Waters e2695
Column: C18 (4.6×250 mm), 5 μm
UV detector: 242 nm
Injection volume: 10 μl
Eluent (gradient)—A: $H_2O+H_3PO_4$, B: acetonitrile Test Example 51

After Test Example 3 was conducted, the filtration loss rate of the reactant (filtrate) was calculated by the following Equation 1.

$$\text{Filtration loss rate (\% by weight)} = (m_1 - m_2/m_1) \times 100 \quad \text{[Equation 1]}$$

$m_1$: Initial weight of the third reactant (the initial weight of the third reactant obtained through depolymerization in the second continuous reactor (CSTR-2) in Examples 1 to 7 and Comparative Examples 1 to 3; and the initial weight of the reactant obtained through depolymerization in the third continuous reactor (CSTR-3) in Comparative Examples 4 to 6)

$m_2$: Weight of the third reactant that has passed through the filtration membrane having a pore size of 0.1 μm (the weight of the third reactant obtained through depolymerization in the second continuous reactor (CSTR-2) that had passed through the filtration membrane having a pore size of 0.1 μm in Examples 1 to 7 and Comparative Examples 1 to 3; and the weight of the reactant obtained through depolymerization in the third continuous reactor (CSTR-3) that had passed through the filtration membrane having a pore size of 0.1 μm in Comparative Examples 4 to 6)

Referring to Table 4, in Examples 1 to 7, in which the preparation process according to the present invention was applied, as depolymerization was carried out through co-extrusion and a kneader, followed by multi-stage depolymerization, depolymerization was carried out in a relatively short time, which minimized the formation of by-products viewed as impurities and produced bis(2-hydroxyethyl) terephthalate with high purity. In addition, as waste PET was well reduced in molecular weight, resulting in almost no residual oligomers, the filtering process for removing unreacted substances and contaminants was efficiently carried out.

In contrast, referring to Table 5, in Comparative Examples 1 to 3, in which the co-extrusion process was not carried out, the reduction in molecular weight of waste PET was not achieved as compared with Examples 1 to 7; thus, residual oligomers increased, and the amount of by-products formed increased. In addition, in Comparative Examples 4 to 6, in which multi-stage depolymerization was carried out without a reduction in molecular weight of the waste PET, resulting

TABLE 4

| | | Ex. 1 | Ex. 2 | Ex. 3 | Ex. 4 | Ex. 5 | Ex. 6 | Ex. 7 |
|---|---|---|---|---|---|---|---|---|
| GPC Area % of the reactant (after kneader) | Monomer | 71.21 | 71.21 | 68.96 | 68.96 | 59.77 | 59.77 | 76.00 |
| | Dimer | 20.92 | 20.92 | 19.84 | 19.84 | 24.12 | 24.12 | 11.93 |
| | Trimer | 6.12 | 6.12 | 5.91 | 5.91 | 8.92 | 8.92 | 2.43 |
| | Oligomer (>Mw 2,000) | 1.76 | 1.76 | 5.29 | 5.29 | 7.19 | 7.19 | 9.64 |
| GPC Area % of the reactant (after CSTR) | Monomer | 91.27 | 91.27 | 82.94 | 91.07 | 89.19 | 90.57 | 89.04 |
| | Dimer | 8.17 | 8.20 | 14.58 | 7.87 | 8.81 | 8.17 | 8.39 |
| | Trimer | 0.54 | 0.53 | 2.26 | 0.66 | 1.01 | 0.62 | 0.88 |
| | Oligomer (>Mw 2,000) | 0.03 | 0.00 | 0.23 | 0.40 | 0.99 | 0.64 | 1.70 |
| Filtering success or not | | ◎ | ◎ | ◎ | ○ | ○ | ○ | ○ |
| Filtering time (min.) | | 6 | 8 | 13 | 20 | 21 | 25 | 28 |
| Filtering flow rate (kg/hr) | | 60.0 | 45.0 | 27.7 | 18.0 | 17.1 | 14.4 | 12.9 |
| HPLC Area of the filtered reactant (filtered crude) (%) | BHET | 88.6 | 88.23 | 87.5 | 86.35 | 86.32 | 85.51 | 85.82 |
| | MHET | 1.2 | 0.96 | 1.55 | 2.07 | 1.47 | 1.19 | 2.11 |
| | DEG-ester 1 | 0.4 | 0.56 | 0.61 | 0.64 | 0.7 | 0.73 | 0.6 |
| | DEG-ester 2 | 0.05 | 0.16 | 0.07 | 0.57 | 0.17 | 0.15 | 0.09 |
| | Dimer | 8.63 | 9.25 | 8.82 | 8.72 | 10.2 | 10.87 | 10.2 |
| | Trimer | 0.61 | 0.64 | 0.65 | 0.67 | 0.71 | 0.82 | 0.69 |
| | Others | 0.51 | 0.20 | 0.80 | 0.98 | 0.43 | 0.73 | 0.49 |
| Filtration loss rate (% by weight) | | 1.40 | 1.10 | 2.30 | 1.90 | 3.80 | 3.60 | 6.00 |

TABLE 5

| | | Com. Ex. 1 | Com. Ex. 2 | Com. Ex. 3 | Com. Ex. 4 | Com. Ex. 5 | Com. Ex. 6 |
|---|---|---|---|---|---|---|---|
| GPC Area % of the reactant (after kneader) | Monomer | 62.22 | 64.74 | 63.44 | — | — | — |
| | Dimer | 15.85 | 17.24 | 19.61 | — | — | — |
| | Trimer | 7.13 | 5.65 | 5.32 | — | — | — |
| | Oligomer (>Mw 2,000) | 14.80 | 12.38 | 11.63 | — | — | — |
| GPC Area % of the reactant (after CSTR) | Monomer | 78.64 | 80.16 | 86.08 | 53.64 | 59.99 | 62.83 |
| | Dimer | 10.54 | 14.28 | 10.30 | 12.89 | 15.97 | 16.44 |
| | Trimer | 3.29 | 2.32 | 1.16 | 3.52 | 4.30 | 5.27 |
| | Oligomer (>Mw 2,000) | 7.53 | 3.24 | 2.46 | 29.95 | 19.73 | 15.46 |
| Filtering success or not | | ○ | ○ | ○ | x | x | x |
| Filtering time (min.) | | 49 | 43 | 39 | 459 | 376 | 210 |
| Filtering flow rate (kg/hr) | | 7.3 | 8.6 | 9.2 | 0.8 | 1.0 | 1.7 |
| HPLC Area of the filtered reactant (filtered crude) (%) | BHET | 85.41 | 85.74 | 85.55 | 82.75 | 81.62 | 83.17 |
| | MHET | 1.68 | 1.37 | 1.09 | 4.89 | 2.69 | 1.81 |
| | DEG-ester 1 | 0.66 | 0.67 | 0.69 | 0.7 | 0.81 | 0.79 |
| | DEG-ester 2 | 0.12 | 0.02 | 0.39 | 0.11 | 0.11 | 0.8 |
| | Dimer | 10.54 | 10.5 | 11.2 | 10.89 | 12.81 | 12.04 |
| | Trimer | 0.83 | 0.73 | 0.87 | 0.73 | 0.73 | 0.91 |
| | Others | 0.76 | 0.97 | 0.21 | 0.04 | 1.23 | 0.48 |
| Filtration loss rate (% by weight) | | 9.70 | 8.70 | 8.00 | 32.80 | 15.80 | 12.70 | in a lot of residual oligomers and a high filtration loss rate; thus, the efficiency of the process for preparing bis(2-hydroxyethyl) terephthalate was significantly deteriorated.

EXPLANATION OF REFERENCE NUMERALS

10: co-extruder
20: agitated shaft reactor
30: first continuous reactor
40: second continuous reactor
The invention claimed is:

1. A process for preparing bis(2-hydroxyethyl) terephthalate, which comprises steps of:
  (1) feeding a waste polyester raw material and a glycol based compound to a co-extruder to obtain a co-extrudate;
  (2) feeding the co-extrudate to an agitated shaft reactor and depolymerizing it to obtain a first reactant;
  (3) feeding the first reactant to a first continuous reactor and depolymerizing it to obtain a second reactant; and
  (4) feeding the second reactant to a second continuous reactor and depolymerizing it to obtain a third reactant,
  wherein, in step (3), a second glycol-based compound is continuously fed to the first continuous reactor in an amount of 50 to 340 parts by weight relative to 100 parts by weight of the first reactant,
  wherein the depolymerization in step (2) is carried out at 180 to 210° C.,
  wherein the depolymerization in step (4) is carried out at 140 to 170° C., and
  wherein a temperature of the depolymerization in step (2) is higher than a temperature of the depolymerization in steps (3) and (4).

2. The process for preparing bis(2-hydroxyethyl) terephthalate of claim 1, wherein a first glycol-based compound is continuously fed to the co-extruder in step (1) in an amount of 0.01 to 100 parts by weight relative to 100 parts by weight of the waste polyester raw material.

3. The process for preparing bis(2-hydroxyethyl) terephthalate of claim 1, wherein the co-extrusion in step (1) is carried out at 170 to 290° C.

4. The process for preparing bis(2-hydroxyethyl) terephthalate of claim 1, wherein the co-extrudate has a weight average molecular weight of 3,000 to 36,000.

5. The process for preparing bis(2-hydroxyethyl) terephthalate of claim 1, wherein the depolymerization in step (2) is carried out for 20 to 50 minutes.

6. The process for preparing bis(2-hydroxyethyl) terephthalate of claim 1, wherein a catalyst comprising a metal acetate or an anhydride or a hydrate thereof is further fed to the agitated shaft reactor in step (2).

7. The process for preparing bis(2-hydroxyethyl) terephthalate of claim 1, wherein the first reactant obtained through step (2) has a peak area fraction of bis(2-hydroxyethyl) terephthalate (BHET) of 50 to 75% as measured by high-performance liquid chromatography (HPLC).

8. The process for preparing bis(2-hydroxyethyl) terephthalate of claim 1, wherein the agitated shaft reactor comprises one or more selected from the group consisting of a kneader, a paddle mixer, a plow shear mixer, a screw mixer, and a ribbon blender.

9. The process for preparing bis(2-hydroxyethyl) terephthalate of claim 1, wherein the third reactant obtained through step (4) has a peak area fraction of bis(2-hydroxyethyl) terephthalate (BHET) of 80 to 90% as measured by high-performance liquid chromatography (HPLC).

10. The process for preparing bis(2-hydroxyethyl) terephthalate of claim 1, wherein the depolymerization in step (3) is carried out at 170 to 195° C. for 30 to 50 minutes.

11. The process for preparing bis(2-hydroxyethyl) terephthalate of claim 1, wherein a third glycol-based compound is continuously fed to the second continuous reactor in step (4) in an amount of 50 to 150 parts by weight relative to 100 parts by weight of the second reactant.

12. The process for preparing bis(2-hydroxyethyl) terephthalate of claim 1, wherein, when the third reactant of step (4) is filtered using a filtration membrane having a pore size of 0.1 μm, the flow rate passing through the filtration membrane is 10 kg/hr or more.

13. The process for preparing bis(2-hydroxyethyl) terephthalate of claim 1, wherein, when the third reactant of step (4) is filtered using a filtration membrane having a pore size of 0.1 μm, the third reactant in step (4) has a filtration loss rate of less than 8% by weight according to the following Equation 1:

$$\text{Filtration loss rate (\% by weight)} = \left(m_1 - m_2/m_1\right) \times 100 \qquad \text{[Equation 1]}$$

$m_1$: Initial weight of the third reactant
$m_2$: Weight of the third reactant that has passed through the filtration membrane having a pore size of 0.1 μm.

14. The process for preparing bis(2-hydroxyethyl) terephthalate of claim 1, which further comprises step (5) purifying the third reactant of step (4).

15. The process for preparing bis(2-hydroxyethyl) terephthalate of claim 2, wherein a third glycol-based compound is continuously fed to the second continuous reactor in step (4) in an amount of 50 to 150 parts by weight relative to 100 parts by weight of the second reactant.

* * * * *